United States Patent
Yamahara

(10) Patent No.: US 6,376,682 B1
(45) Date of Patent: Apr. 23, 2002

(54) COMPOUND WITH α-GLUCOSIDASE INHIBITING ACTION AND METHOD FOR PRODUCING THE SAME

(75) Inventor: Johoji Yamahara, Otu (JP)

(73) Assignee: Takama System, Ltd., Yamaguchi (JP)

( * ) Notice: Subject to any disclaimer, the term of this patent is extended or adjusted under 35 U.S.C. 154(b) by 0 days.

(21) Appl. No.: 09/773,652

(22) Filed: Jan. 31, 2001

Related U.S. Application Data

(62) Division of application No. 09/495,568, filed on Feb. 1, 2000, now abandoned.

(51) Int. Cl.$^7$ .................... C07D 333/32; A61K 31/38
(52) U.S. Cl. .................... 549/66; 549/62; 514/445
(58) Field of Search ............. 549/66, 62; 514/445

(56) References Cited

U.S. PATENT DOCUMENTS 5,691,386 A * 11/1997 Inman et al. ............. 514/691

OTHER PUBLICATIONS

Yoshikawa, Masayuki et al, "Salacinol, potent antidiabetic principle with unique thiosugar sulfonium sulfate structure from the ayurvedic traditional medicin Salacia Reticulata in Srilanka and India", Tetrahedron Letters, vol. 38, No. 48, pp. 8367–8370, 1997.*

* cited by examiner

*Primary Examiner*—Deborah C. Lambkin
(74) *Attorney, Agent, or Firm*—Koda & Androlia

(57) ABSTRACT

A compound expressed by chemical structural formula:

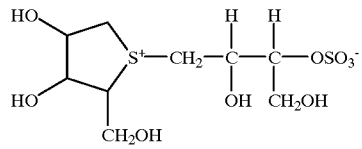

having the characteristic of specifically inhibiting the activity of α-glucosidase (an enzyme that breaks down disaccharides, etc.) at the intestinal level. The compound is obtained by extraction and fractionation from *Salacia prinoides* and/or *Salacia oblonga*, which are used as natural drugs. A highly safe antidiabetic agent and dieting agent are produced using the compound as a base.

5 Claims, 2 Drawing Sheets

# COMPOUND WITH α-GLUCOSIDASE INHIBITING ACTION AND METHOD FOR PRODUCING THE SAME

This Appln is a Div. of Ser. No. 09/495,568 Feb. 1, 2000.

BACKGROUND OF THE INVENTION

1. Field of the Invention

The present invention relates to a novel compound obtained from a natural plant and more particularly to a compound which is extracted from a woody climbing plant belonging to the Celastaceae family and inhibits the activity of α-glucosidase, and further to an antidiabetic and dieting agent containing the compound and a method for producing such a compound.

2. Prior Art

In recent years, among therapeutic drugs classified as antidiabetic agents, α-glucosidase inhibitors which inhibit the activity of α-glucosidase have been widely used in the treatment of diabetes and prediabetes. α-glucosidase is an enzyme that breaks down disaccharides or Strisaccharides and glucides such as starch, etc., that are present on the mucous membranes of the digestive tract.

As universally known, natural medicines and medicinal foodstuffs, which can be safely and easily supplied in the diet and can inhibit the onset of hyperglycemia, are constantly in demand.

Accordingly, natural drugs used in various traditional systems of medicine around the world have attracted attention as a means of developing natural medicines that do not originate in chemically synthesized products.

In research and development for developing such natural medicines, the inventor of the present invention has made special efforts in the development of antidiabetic agents.

In this research, the inventor has focused special attention on *Salacia reticulate*. *Salacia reticulata* belongs to the Celastaceae family, known in Singhalese as *Kotala himbutuwel*, which has been used since ancient times in the traditional medicine of India and Sri Lanka, i.e. in the Ayurvedic medical tradition. In rat experiments by the inventor, an aqueous extract (watersoluble fraction) of this substance has shown a superior effect in inhibiting hyperglycemia following sucrose or maltose loading (i.e., this substance has strongly inhibited the increase of blood sugar levels after the administration of sucrose or maltose in rats). In other words, the inventor has ascertained that the above-described extract is effective in inhibiting the activity of α-glucosidase, an enzyme that as described above breaks down disaccharides, etc.

Furthermore, the inventor has also ascertained that an aqueous extract of *Salacia reticulata* belonging to the Celastaceae family inhibits the activity of α-glucosidase, i.e., maltase and sucrase, present in the intestines of rats (the fraction inhibited rat intestinal maltase and sucrase).

Furthermore, the present inventor is investigating the active principle that manifests the hyperglycemia-inhibiting effect in *Salacia reticulata* of the Celastaceae family.

The inventor has also screened plants other than *Salacia reticulata*, which is a plant belonging to the above-described Celastaceae family, in a search for plants that inhibit the activity of α-glucosidase.

SUMMARY OF THE INVENTION

As a result, the inventor discovered that there is an extremely strong α-glucosidase inhibiting effect in aqueous extracts of *Salacia prinoides* and *Salacia oblonga* belonging to the Celastaceae family, and especially in an aqueous extract of the former plant.

More specifically, the inventor, by extracting and fractionating *Salacia prinoides*, succeeded in discovering a novel compound which has an inhibitory effect against isomaltose (a type of disaccharide) that is more than 200 times stronger than that of the α-glucosidase inhibiting agent Acarbose (manufactured by Bayer Corp., Trademark Glucobay), which is a commercially marketed drug. The Acarbose is a type of sugar that is, like antibiotics, produced by the genus Actinoplanes (a certain type of Actinomyces).

The present invention was created based upon these findings.

Accordingly, the object of the present invention is to provide a novel compound which is extracted from the woody climbing plants *Salacia prinoides* and *Salacia oblonga* and is superior in terms of its characteristic of inhibiting the activity of α-glucosidase (hereafter this compound may be referred to as an "α-glucosidase inhibitor").

Another object of the present invention is to provide an antidiabetic agent or dieting agent which utilizes the above-described compound having the effect in inhibiting α-glucosidase (which is an enzyme that breaks down disaccharides, etc. that are present on the mucous membranes of the digestive tract).

Still another object of the present invention is to provide a method for producing or extracting the above-described compound that has the superior characteristics of inhibiting α-glucosidase activity.

In the present invention, the above-described novel compound (α-glucosidase inhibitor) that has the superior characteristic of inhibiting α-glucosidase activity is obtained by extraction and fractionation from plants belonging to the natural plant Celastaceae family, i.e., *Salacia prinoides* and/or *Salacia oblonga*, which have been utilized as natural drugs. Accordingly, the present invention provides an antidiabetic agent and dieting agent that are superior in terms of safety compared to chemically synthesized products.

More specifically, the present invention provides the compound itself that is expressed by the Chemical Structural Formula shown below, which was discovered in the woody climbing plants *Salacia prinoides* or *Salacia oblonga*. In the following description, the compound expressed by the Chemical Structural Formula shown below may be referred to as the "novel compound SP (SP merely called after *Salacia Prinoides*)".

Chemical Structural Formula

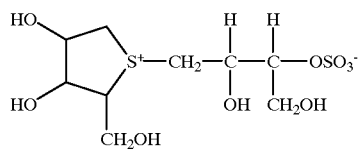

Furthermore, the present invention provides an antidiabetic agent which utilizes the property of effectively inhibiting the activity of α-glucosidase (an enzyme that breaks down disaccharides, etc.) shown by the compound expressed by the above Chemical Structural Formula The present invention further provides a dieting agent used to prevent obesity caused by excessive nutrition, which utilizes the α-glucosidase inhibiting effect of the compound shown by the above Chemical Structural Formula in order to prevent the breakdown of various types of glucides and oligosaccharides (disaccharides or trisaccharides) ingested in meals into monosaccharides and the absorption of such monosaccharides in the body. These applied products were not known at the time of the previous research and development work concerning *Salacia reticulata*.

Moreover, the present invention provides a method for extracting the novel compound expressed by the above Chemical Structural Formula which is superior in terms of its characteristic of inhibiting the activity of α-glucosidase. In this method, *Salacia prinoides* and/or *Salacia oblonga* of the Celastaceae family are subjected to an extraction process using heated methanol, the methanol extract thus obtained are subjected to a partition treatment using ethyl acetate and water, and the portion migrating into the water is then subjected to a fractionation treatment by means of chromatography.

DETAILED DESCIPTION OF THE PREFERRED EMBODIMENTS

Figure 1:
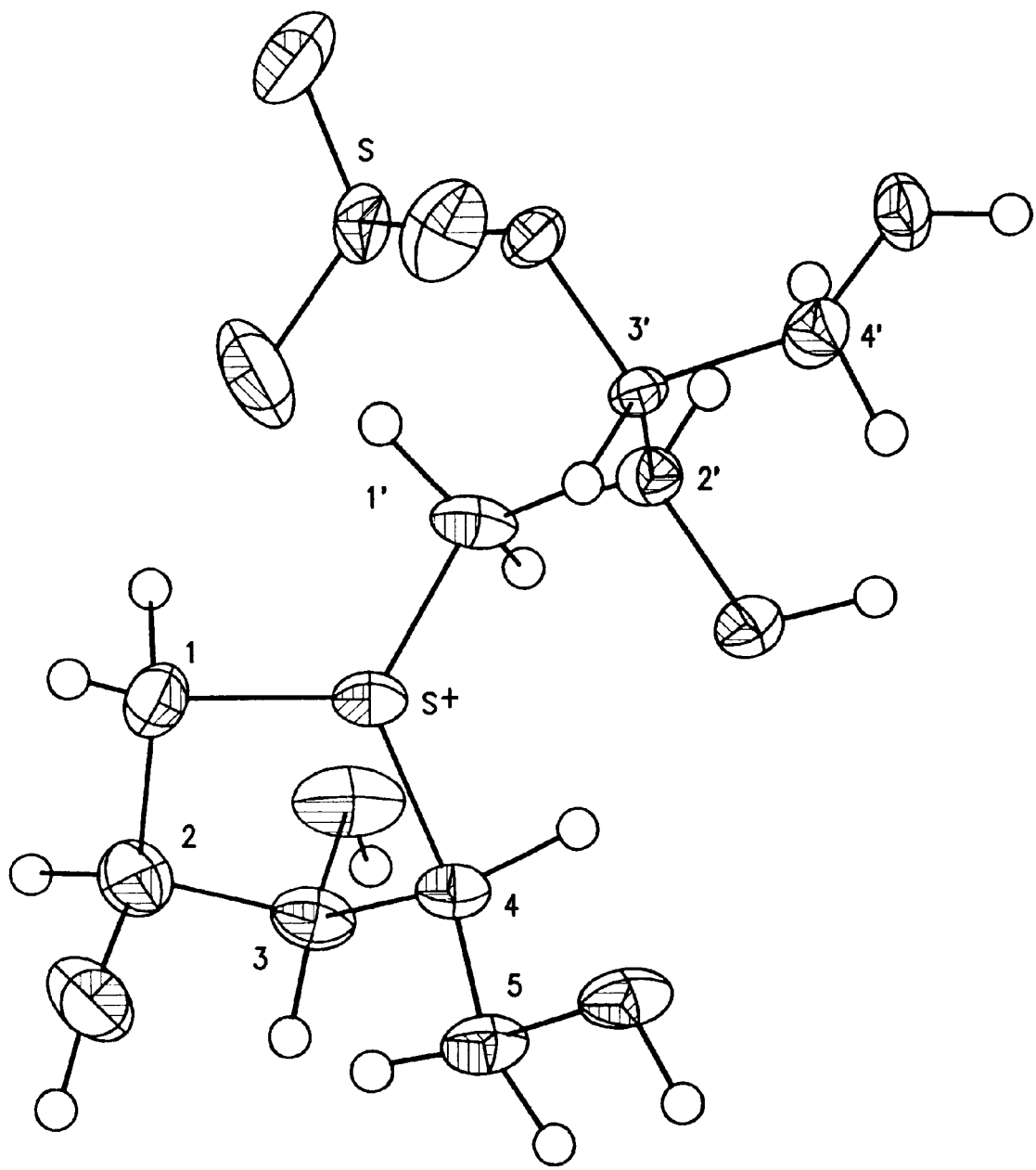
FIG. 1 is an X-ray analysis diagram of the novel compound SP according to the present invention.

The present invention will be described in detail below.

As described above, the object of the present invention is to discover the true compound that inhibits the activity of α-glucosidase (which is an enzyme that breaks down disaccharides, etc.) by applying extraction and fractionation processes using, as a basis, *Salacia prinoides* and/or *Salacia oblonga* that belong to the Celastaceae family (whose plants are used as components of natural medicines). It is another object of the present invention to provide a safe and highly potent antidiabetic agent and dieting agent of the natural drug type which use, as a basis, the thus discovered novel compound (that shows superior inhibition of α-glucosidase activity).

In research and development aimed at discovering the active principle (active substance) that inhibits the activity of α-glucosidase using *Salacia prinoides* and/or *Salacia oblonga* of the Celastaceae family as a base, the present inventor succeeded in discovering the novel compound SP expressed by the Chemical Structural Formula shown as:

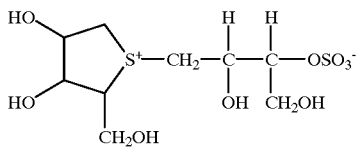

Further, the inventor succeeded in developing an antidiabetic agent and a dieting agent that uses the properties of the novel compound SP which is the above-described active principle (active substance), and also in establishing an effective and economical method for extracting the novel compound S.

The novel compound SP of the present invention which is expressed by the above Chemical Structural Formula has the property of effectively inhibiting the activity of α-glucosidase, and is useful as an antidiabetic agent. In other words, the novel compound SP of the present invention inhibits the breakdown of oligosaccharides (disaccharides and trisaccharides) such as sucrose, maltose, etc. into monosaccharides that is caused by α-glucosidase, and inhibits the absorption of monosaccharides such as glucose, mannose, etc. in the body, so that blood sugar levels are prevented form rising. Accordingly, the compound of the present invention is extremely useful as an antidiabetic agent.

Furthermore, since the novel compound SP of the present invention inhibits the activity of α-glucosidase which is an enzyme that breaks down glucides such as starch, etc. and oligosaccharides (disaccharides and trisaccharides), the compound prevents the breakdown of glucides and oligosaccharides into monosaccharides such as glucose, etc. Accordingly, the absorption of excessive glucose in the body is prevented. As universally known, glucose absorbed in the body is converted into glycogens and neutral lipids by insulin and then accumulates as body fat or organ fat, thus causing obesity. As is clear from the above description, the novel compound SP of the present invention is extremely useful as a dieting agent. The novel compound SP can also be obtained by extraction and fractionation from *Salacia reticulata*.

In the present invention, the novel compound SP expressed by the above Chemical Structural Formula can be prepared as a crystalline material. Accordingly, the powdered compound itself, or a mixture of the compound with some other appropriate excipient, milk sugar, starch, etc., can be formed into tablets, granules, etc. and used in this form.

Furthermore, the novel compound SP of the present invention can also be used as an additive which is added in very small amounts to gum or chocolate or to high-starch breads, noodles, confections, etc.

In addition, the novel compound SP of the present invention can be obtained by subjecting plants of the genus Salacia to an extraction using a desired medium. The thus obtained extract (including brew, steeping liquid or decoction) containing the novel compound SP can be used "as is", and such an extract can be also used after concentrating it into a concentrated liquid. Alternatively, the extract can be subjected to evaporative drying so as to be in a solid powder form. For example, the novel compound SP of the present invention can be used in the form of a liquid agent (such as an aqueous solution, etc.) as an antidiabetic agent or dieting agent.

The extract can be prepared from plants of the above-described genus Salacia by performing an extraction operation in any desired manner.

For example, the raw material is crudely cut or pulverized to approximately 30 mesh by means of a pulverizer. Next, 51 liters of water, alcohol or water-containing alcohol is added as a solvent to 1 kg of the pulverized plant material, and this mixture is allowed to stand for three hours at 80 to 90° C., in the case of hot steeping (or extraction), or for three days at room temperature in the case of cold steeping (or extraction). Then, the resulting mixture is filtered, and the solvent is completely removed from the filtrate at 45° C. under reduced pressure, so as to prepare a dried extract solid. Then, in order to form into a powdered formulation, the extract solid is powdered to approximately 100 to 150 mesh.

In regard to the amount used of the novel compound SP of the present invention expressed by the above Chemical Structural Formula, the dosage varies according to age, symptoms, etc. in cases where the compound is used as an antidiabetic agent or dieting agent. For adults, a tentative standard is 5 to 10 mg per dose 15 to 30 minutes before meals.

Furthermore, in regard to the amount of addition of the novel compound SP to food products, a tentative standard is 0.01 to 0.005 wt %.

Examples

Below, the present invention will be described in greater detail by way of examples. It goes without saying that the present invention is not limited to the following embodiments.

(1) Extraction and Fractionation 1.7 kg of *Salacia prinoides* (portion above ground) was subjected to an extraction (for three hours) with 71 liters of methanol while being heated to a temperature of 90 to 95° C. Afterward, the extract was collected by filtration.

Next, 71 liters of methanol was added to the extraction residue, and a similar extraction operation was performed a total of three times.

Then, the filtrates obtained by the extraction operations were combined, and the solvent was completely distilled away under reduced pressure, thus producing 139 g of a methanol extract. The yield was 8.2%.

Lastly, 130 g of the methanol extract thus obtained was partitioned using ethyl acetate: water (1:1); in both migrating portions, the solvent was completely distilled away under reduced pressure, thus producing 23 g of a portion that migrated into ethyl acetate and 107 g of a portion that migrated into water.

(2) Fractionation of Portion that Migrated into Water 50 g of the above-described portion that migrated into water was dissolved in methanol, thus producing 41 g of a methanol-soluble portion and 8.6 g of an insoluble portion.

Next, 31 g of the portion that migrated into methanol was subjected to sequential-phase silica gel column chromatography (silica gel: 1.5 kg), with solvents introduced as shown below, thus producing fractions 1 through 8.

(i) The solvents were introduced as follows:

Chloroform: methanol: water (6:4:1 →5:5:1 →3:7:1) →methanol →50% acetone.

(ii) The yields of the respective fractions were as follows:

Fraction 1 (1.8 g), fraction 2 (1.2 g), fraction 3 (2.5 g), fraction 4 (3.7 g), fraction 5 (4.0 g), fraction 6 (13.5 g), fraction 7 (0.9 g), fraction 8 (0.7 g).

(3) Re-Fractionation of Fraction 3

The inhibiting effect (inhibitory power: $IC_{50}$ value) on sucrase, which is a type of α-glucosidase, was investigated for each fraction.

"Fraction 3", which showed an especially strong inhibiting effect, was further separated and purified as shown below.

Specifically, separation and purification were repeated under the conditions shown below, using high-performance liquid chromatography (HPLC).

Column conditions: Shodex SC 1011 ($Ca^{2+}$), 8 i.d. ×300 mm.

Solvent: water, Temperature: 80° C., Flow rate: 0.7 ml/min.

Under the above-described column conditions, six fractional components, i.e., "fraction 3-1" through "fraction 3-6", were obtained from "fraction 3".

Next, using 36 mg of "fraction 3-3" (137 mg), which showed an especially high activity among the above-described fractional components, separation and purification were performed as shown below by means of high-performance liquid chromatography (HPLC).

Column conditions: YMC-Pak, polyamine II, 10 i.d.×250 mm.

Solvent: 25% aqueous solution of acetonitrile, Flow rate: 5.0 ml/min.

As a result, 8.7 mg of D-(+) glucose, 4.2 mg of sucrose and 3.0 mg of the novel compound SP were obtained.

Furthermore, using 220.0 mg of "fraction 3-4" (249.7 mg), which showed a relatively high activity, separation and purification were performed as shown below by means of highperformance liquid chromatography (HPLC).

Column conditions: Shodex SO 810 ($Pb^{2+}$), 8 i.d.×300 mm.

Solvent: water, Temperature: 80° C., Flow rate: 0.6 ml/min.

Under the above-described column conditions, three fractional components, i.e., "fraction 3-4-1" through "fraction 3-4-3", were obtained from "fraction 3-4".

Next, using 18 mg of the high-activity "fraction 3-4-3" (73.5 mg) obtained by the above-described separation and purification, separation and purification were further performed as follows by means of high-performance liquid chromatography (HPLC).

Column conditions: YMC-Pak, polyamine II, 10 i.d.×250 mm.

Solvent: 25% aqueous solution of acetonitrile, Flow rate: 5.0 ml/min.

As a result, 2.5 mg of the same novel compound SP was obtained.

Table 1 summarizes the above-described fractionation scheme and the inhibiting effects (inhibitory power: $IC_{50}$ value) of the respective fractional components on sucrase.

TABLE 1

Fractionation Scheme and Sucrase Inhibiting Activity of Respective Fractions ($IC_{50}$ values)

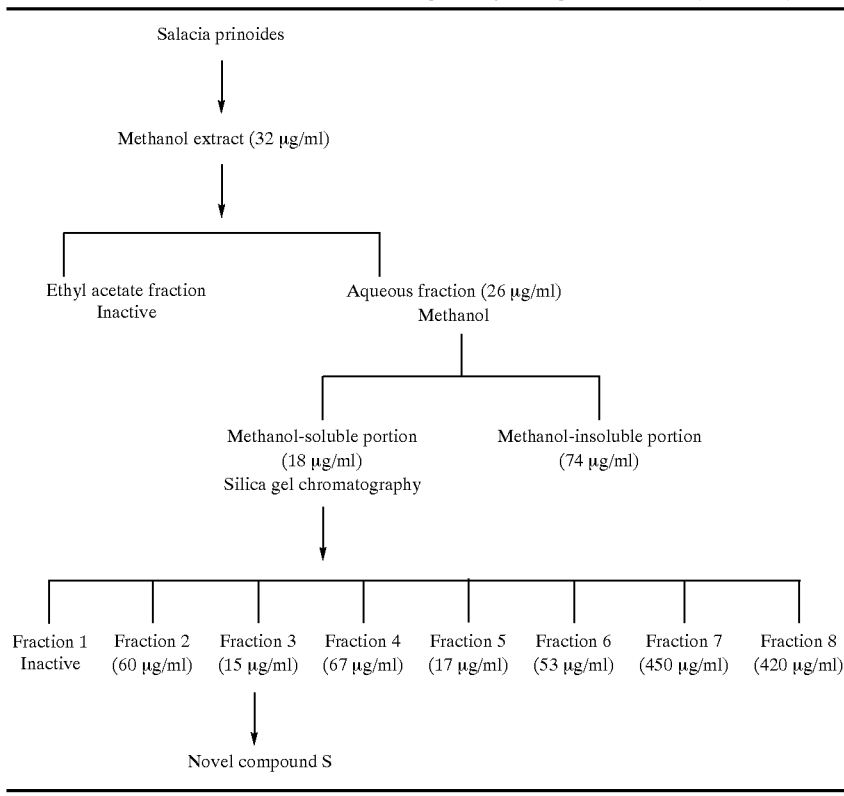

In the present invention, the above-described method for extracting and fractionating *Salacia prinoides* should be viewed as the optimal configuration from the standpoints of extraction efficiency and efficiency of removal of inactive portions, etc.

Various modifications are possible in the method used to extract and fractionate *Salacia prinoides*. For example, in the extraction process, some other solvent such as water or an alcohol other than methanol may be used instead of the methanol. Furthermore, in the process to remove inactive components (inactive component partition process), chloroform/water, for example, may be used instead of the partition process that uses ethyl acetate/water.

(4) Determination of Structure of Novel Compound S

The structure of the novel compound SP separated and purified as described above was determined.

More specifically, an empirical formula was determined by determining the composition of the novel compound SP by means of elemental analysis using an ordinary method, and the molecular formula was determined by separately measuring the molecular weight.

Next, X-ray diffraction was performed in order to determine the structural formula indicating the arrangement of the atomic bonds in the molecule.

In addition, specific rotation measurements, mass analysis and analysis of the infrared absorption spectrum (IR) and nuclear magnetic resonance spectrum (NMR) were also performed.

The results obtained are shown below. In the following description, the symbol A stands for "angstrom" ($1 \times 10^{-8}$ cm).

(i) Molecular formula: $C_9H_{18}S_2O_9$ (ii) Molecular weight: MW=334.36

(iii) X-ray diffraction:

(iii-1) X-ray diffraction was performed under the following conditions:

| | |
|---|---|
| X-ray diffraction apparatus: | AFC5R manufactured by Rigaku K.K. |
| Radiation: | MoKα (λ = 0.71069 A) |
| Temperature: | 23° C. |
| Attenuators: | Ni foil (factors: 3.6, 12.0, 42.0) |
| Take-off angle: | 6.0° |

(iii-2) The X-ray diffraction data (crystal data) was as follows:

| | |
|---|---|
| Crystal color, habit: | colorless, prisms |
| Size of crystals (mm): | 0.150 × 0.200 × 0.200 |
| Crystallographic type: | monoclinic |

Number of reflections used for unit cell determination (2θ range, crystal reaction intensity): 25 (46.6 to 49.5°)

Omega scan peak width at half-height: 0.36

| | |
|---|---|
| Lattice parameters: | a = 6.433 (3) A |
| | b = 12.927 (2) A |
| | c = 8.372 (3) A |
| | β = 93.680 (3) A |

-continued

| | |
|---|---|
| | V = 694.800 (4) A$^3$ |
| Space group: | P2 (#4) |
| Z-value: | 2 |
| Dm: | 1.598 g/cm$^3$ |
| F (000): | 352 |
| μ (MoKα): | 4.05 cm$^{-1}$ |

The X-ray analysis diagram produced by the X-ray diffraction is shown in FIG. 1.

Figure 2:
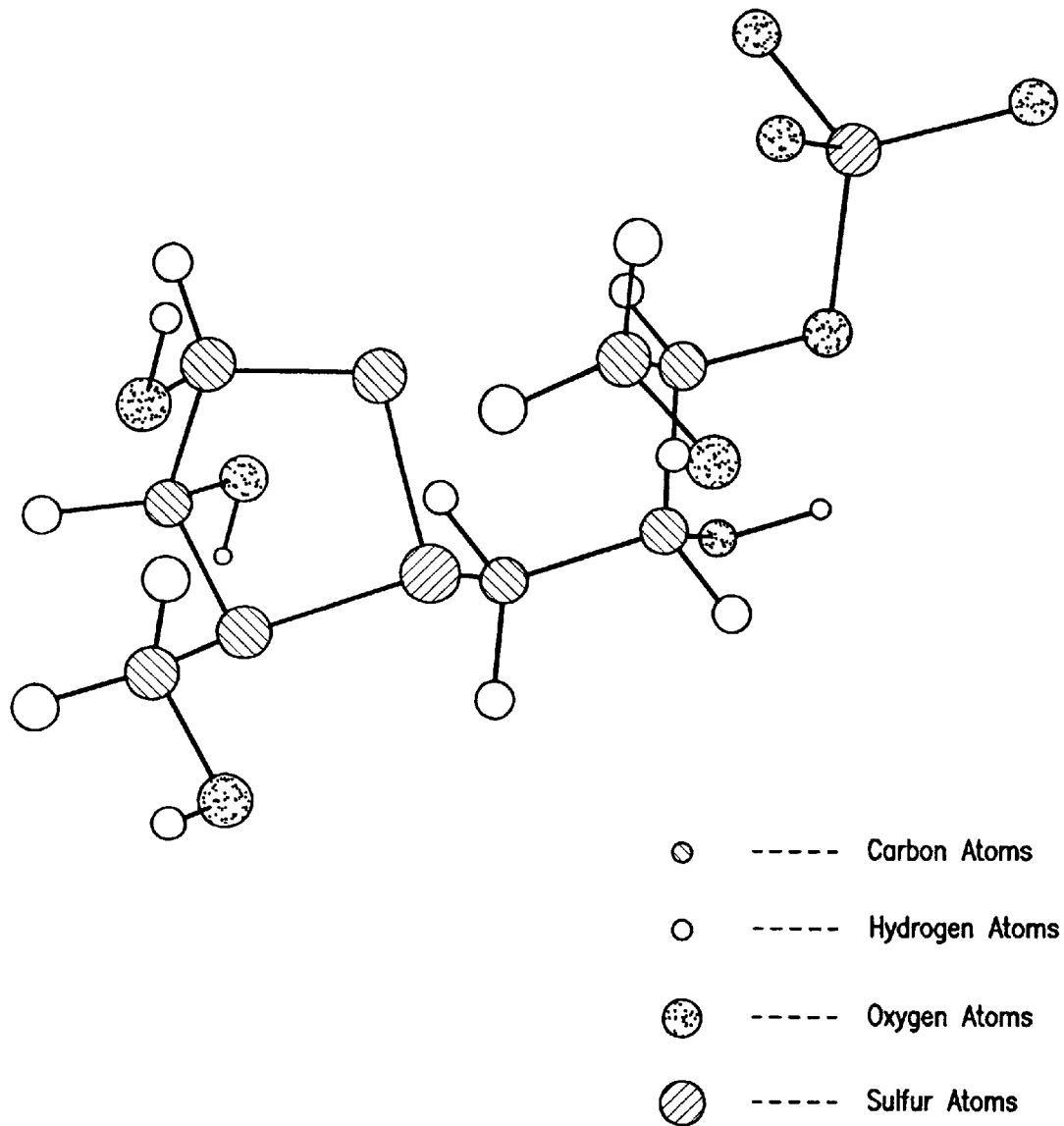
FIG. 2 is a model diagram of the novel compound SP according to the present invention.

Furthermore, a model diagram which makes the above-described X-ray analysis diagram in FIG. 1 easier to comprehend in visual terms is shown in FIG. 2.

In the present invention, structural analysis of the novel compound SP was also performed by means other than the X-ray analysis. Physical and chemical data for the novel compound SP obtained by these other analysis methods are shown below.

1. Measurement of Specific Rotation:

The measurement results obtained for specific rotation were as follows:

$[\alpha]_D^{28}$=+4.9° (C=0.35, MeOH)

2. Mass Analysis:

The mass analysis results were as follows:

The analysis results obtained by high-resolution secondary ion mass analysis, i.e., high-resolution SIMS (m/z), were as follows:

(i) Calculated value: (note) $C_9H_{19}S_2O_9(M+H)^+$= 335.0469.

(ii) Experimental value: 335.0463.

3. Infrared Absorption Spectrum (IR) Analysis:

The IR (KBr) analysis results were as follows:

IR (KBr): 3417 (—OH), 1261 and 1237 (—OSO$_3^-$), 1072 and 1018 (—CO—, —CS—), 801.

4. $^1$H-NMR Analysis:

The $^1$H-NMR analysis results were as follows:

$^1$H-NMR (500 MHz, pyridine-d$_5$): 4.31 (2H, br s, 2-H$_2$), 4.35, 4.58 (1H each, both dd, J=3.7, 11.6 Hz, 4'-H$_2$), 4.50(2H, m, 6-H$_2$), 4.60, 4.77 (1H each, both dd, J=4.6, 13.2 Hz, 1'-H), 4.67(1H, dt, J=6.4, 6.7Hz, 5-H), 4.97(1H, m, 2'-H), 5.09(2H, br s, 2, 3-H), 5.24 (1H, dt, J=3.7, 7.7Hz, 3'-H).

The spatial arrangement of H (hydrogen atoms) is shown in the X-ray analysis diagram (FIG. 1).

5. $^{13}$C-NMR Analysis:

The $^{13}$C-NMR analysis results were as follows:

$^{13}$C-NMR (125 MH): 50.5(2-C), 52.8(1'-C), 60.2(6-C), 62.3(4'-C), 67.6(2'-C), 78.3(3-C), 79.2(3'-C), 79.3(2-C).

The spatial arrangement of C (carbon atoms) is shown in the X-ray analysis diagram (FIG. 1).

According to the above structural analysis, the novel compound SP of the present invention has the above-described Chemical Structural Formula. Furthermore, as shown in 4-thiorabinofuranosyl cation and a 1'-deoxyerythrosyl-3'-sulfate anion, which has a unique spiral-like configuration.

Next, characteristics and application examples of the novel compound SP of the present invention will be described below.

(i) Activity inhibiting effect on enzymes that break down glucides:

(i-1) Preparation of Enzymes

The brush border membrane obtained from the jejunum of male Wistar rats (body weight: 150 to 350 g) was used as a crude enzyme.

The brush border membrane was suspended in a 0.01 M maleic acid buffer solution (pH=6.0), and this suspension was diluted to a concentration at which the substrate was hydrolyzed at the rate of approximately 25 to 50 n/mol/ml/minute.

The reason that the brush border membrane was selected as the crude enzyme is that this brush border membrane contains large amounts of α-glucosidase such as maltase, sucrase, isomaltase, etc.

(i-2) Test Method

For maltase, sucrase and isomaltase, 100 μL of various concentrations of the test drug was added to 50 μL of respective 74 mM maltose, sucrose and isomaltose (used as substrates), and the resulting preparations were pre-heated for 2 to 3 minutes at 37° C.

Next, 50 μL of the enzyme solution was added, and a reaction was performed for 30 minutes. The reaction was stopped by adding 800 μL of water, and placing the reaction mixture in a water bath at 92 to 97° C. for 2 minutes.

The amount of glucose produced was measured by the glucose oxidase method (Glucose CII Test Wako).

In the above, the substrates and test drug were both dissolved in a maleic acid buffer solution (pH=6.0) prior to use.

The results obtained are shown in Table 2 below.

Table 2 shows the inhibiting effects (inhibitory power: IC$_{50}$ value) of the novel compound SP (product of the present invention) and Acarbose (conventional product) on maltase, sucrase and isomaltase (enzymes which break down disaccharides) originating in the small intestines of rats.

TABLE 2

Inhibiting Effects (IC$_{50}$ values) of SP and Acarbose on Maltase, Sucrase and Isomaltase (enzymes which break down disaccharides) Originating in the Small Intestines of Rats.

| Substrate | SP (product of the present invention) | Acarbose (conventional product) |
|---|---|---|
| Maltose (37 mM) | 3.3 | 1.3 |
| Sucrose (37 mM) | 0.84 | 1.1 |
| Isomaltose (3.7 mM) | 0.51 | 100.0 |

(ii) Activity inhibiting effect on β-glucosidase:

This test was performed in order to demonstrate that the novel compound SP of the present invention has a specific activity for α-glucosidase only.

(ii-1) Preparation of Enzyme

β-glucosidase originating in almonds (manufactured by Sigma Co.) was dissolved in a 0.1 M acetic acid buffer solution (pH=5.0), and this solution was diluted to a concentration at which the substrate was hydrolyzed at the rate of 5 n/mol/ml/minute.

(ii-2) Test Method

100 μL of the test drug was added to 50 μL of 10 mM p-nitrophenol-β-D-glycopyronoside (manufactured by Sigma Co.) used as a substrate, and this mixture was preheated for 5 minutes at 37° C.

Next, 50 μL of the enzyme solution was added, and a reaction was performed for 15 minutes. The reaction was stopped by adding 200 μL of a 0.2 M sodium carbonate solution.

The amount of p-nitrophenol produced was determined from the absorbance at 400 nm.

The substrate and test drug were both dissolved in a 0.1 M acetic acid buffer solution (pH=5.0) prior to use.

As a result of the above test, it was ascertained that the novel compound SP of the present invention has no activity inhibiting effect on β-glucosidase.

(iii) Inhibiting effect on hyperglycemia in the case of sucrose loading:

The test was oraly administered as an aqueous solution to fasting male Wistar rats (body weight: 130 to 170 g.

Next after 30 minutes, the sucrose was orally administered to the rats.

Then, 30 minutes, after the administered of the sugar, 0.4 ml of blood was taken from the neck artery of each animal with the animal under restraint without anesthesia (during blood collection only). following colling with ice water, the blood serum was separated by centrifuging, and the glucose concentration (blood sugar level) was measured by the glucose oxidase method (Glucose CII Test Wako).

The above-described test was performed for the novel compound SP (product of the present invention) and Acabose(clnventional roduct).

The results obtained are shown in Table 3 below.

As shown in Table 3, the noval compond SP (product of the present invention) showed a stronger effect in inhibiting the elevation of blood sugar levels than Acarbose (conventional product) did.

TABLE 3

Effects of SP and Acarbose in Inhibiting Blood Sugar Elevation Caused by Sucrose Loading.

| Compound name | Dosage mg/kg, po | Rate of inhibition of blood sugar elevation 30 minutes |
| --- | --- | --- |
| Novel compound SP (product of the present invention) | 5 | 40.5 ± 2.3 |
| | 10 | 62.1 ± 3.8 |
| | 25 | 89.1 ± 3.5 |
| Acarbose (conventional product) | 5 | 33.4 ± 6.2 |
| | 10 | 48.5 ± 6.9 |
| | 25 | 73.8 ± 5.2 |

(iv) Dieting Effect 250 ml of a steeped liquid preparation (a brew) of *Salacia prinoides* (containing approximately 5 mg of the novel compound SP) was given to 10 persons suffering from obesity (average body weight: 72 kg) approximately 10 to 30 minutes before meals.

The above-described administration test was conducted for three months (90 days). As a result, an average weight loss of 5.5% (maximum weight loss: 15%) was observed. The loss of body weight was due mainly to a reduction in the amount of body fat and organ fat.

The above-described dieting effect was also similarly observed in steeped liquid preparations of *Salacia oblonga* and *Salacia reticulata*.

As seen from the above, the novel compound SP of the present invention, which is expressed by the Chemical Structural Formula:

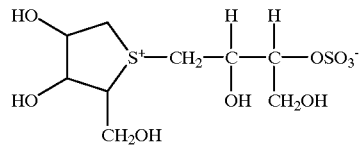

and which is obtained by extraction and fractionation from *Salacia prinoides* and/or *Salacia oblonga*, has the characteristic of speifically inhibiting the activity of α-glucosidase (an enzyme which breaks down disaccharides, etc.) at intestinal levels. Accordingly, this compound can effectively inhibit the production of monosaccharides, which cause high blood sugar levels.

Furthermore, the novel compound SP of the present invention is a component that originates in a natural drug that has been used since ancient times. Accordingly, this compound is highly safe and shows a sufficient effect when administered at the rate of a few milligrams.

Thus, the novel compound SP of the present invention is extremely effective as a drug for inhibiting postprandial hyperglycemia, which is currently a major problem. In other words, this compound is extremely effective as an antidiabetic agent (i.e., an agent which combats diabetes mellitus).

Moreover, the novel compound SP of the present invention effectively inhibits the activity of α-glucosidase whch is an enzyme that breaks down glucides such as starch, and oligosaccharides (disaccharides and trisaccharides). Accordingly, the breakdown of such glucides and oligosaccharides into monosaccharides is prevented, and the absorption of excess glucose in the body is prevented. As a result, by taking the compound of the present invention prior to meals, the absorption of glucose is inhibited, and postprandial hyperglycemia is eliminated. At the same time, necessary energy is obtained by the consumption of accumulated body fat and organ fat in the body. Thus, the compound has a dieting effect.

What is claimed is:

1. A method for manufacturing a compound that has an α-glucosidase inhibiting effect consisting of the steps of performing an extraction on one or more selected from the group consisting of *Salacia prinoides* and *Salacia oblonga* belonging to the Celastaceae family, said compound being expressed by chemical structural formula:

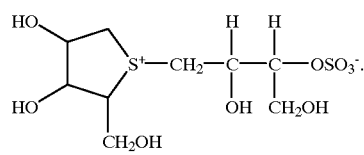

2. The method according to claim 1, wherein a solvent used for said extraction is one selected from the group consisting of water, methanol and water-containing methanol.

3. A method for extracting a compound that has an α-glucosidase inhibiting effect and is expressed by chemical structural formula:

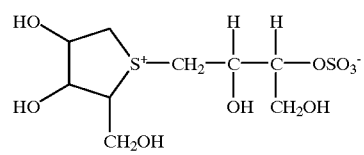

which is characterized in that said method consists of the steps of:

performing an extraction on *Salacia prinoides* belonging to the Celastaceae family by means of heated methanol, thus obtaining methanol extract;

performing a partition treatment on said methanol extract using ethyl acetate and water; and performing a fractionation treatment by chromatography on a portion of said extract that has migrated into said water.

4. A method for using compound as an antidiabetic agent, said compound being obtained by the method of claim 1, having an α-glucosidase inhibiting effect and being expressed by chemical structural formula shown as:

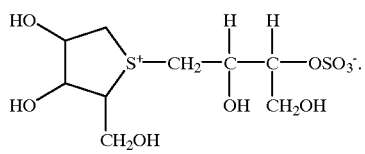

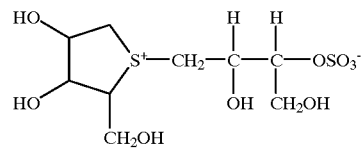

5. A method for using a compound as a dieting agent, said method comprising the steps of ingesting said compound having an α-glucosidase inhibiting effect and expressed by chemical structural formula shown as:

which is obtained from an extract of at least one plant selected from the group consisting of *Salacia prinoides*, *Salacia oblonga* and *Salacia reticulata* which belong to the Celastaceae family.

* * * * *